United States Patent [19]
Orth

[11] Patent Number: 5,981,797
[45] Date of Patent: Nov. 9, 1999

[54] PREPARATION OF DIAMINE CARBAMATES

[75] Inventor: John Harry Orth, Hockessin, Del.

[73] Assignee: E. I. du Pont de Nemours and Company, Wilmington, Del.

[21] Appl. No.: 09/125,093

[22] PCT Filed: Feb. 4, 1997

[86] PCT No.: PCT/US97/01800

§ 371 Date: Aug. 4, 1998

§ 102(e) Date: Aug. 4, 1998

[87] PCT Pub. No.: WO97/29083

PCT Pub. Date: Aug. 14, 1997

Related U.S. Application Data

[60] Provisional application No. 60/011,246, Feb. 6, 1996.

[51] Int. Cl.$^6$ .............................. C07C 51/15; C07C 61/08
[52] U.S. Cl. ............................ 562/550; 562/507; 562/555
[58] Field of Search .................................. 562/507, 550, 562/555

[56] References Cited

U.S. PATENT DOCUMENTS 4,102,801  7/1978  Brodoway ................. 252/182

OTHER PUBLICATIONS

Database CAPLUS on STN, Acc. No. 1973:495899, 'Foundry core binder composition.' FR 2142702 A2, (Abstract), 1973.
Leon Segal, *Applied Spectroscopy*, 17, No. 1, 21–22, 1963.

*Primary Examiner*—Paul J. Killos
*Assistant Examiner*—Brian J. Davis

[57] ABSTRACT

Diamine carbamates are prepared by spraying liquid diamine into carbon dioxide gas, in the optional presence of a propellant.

8 Claims, No Drawings

PREPARATION OF DIAMINE CARBAMATES

This Appln claims the benefit of U.S. Provisional No. 60/011,246 filed Feb. 6,1996.

FIELD OF THE INVENTION

This invention relates to an improved process for the preparation of diamine carbamates by contacting a liquid diamine with carbon dioxide gas.

TECHNICAL BACKGROUND

Polyamine carbamates have been produced in the past by adsorbing the polyamine on a particulate carrier and then reacting the polyamine with carbon dioxide. See Brodoway U.S. Pat. No. 4,102,801.

Another route to carbamate salts is to react an amine in solution with gaseous or dissolved carbon dioxide.

Hexamethylene diamine carbamate has been prepared by the known process of reacting hexamethylene diamine and carbon dioxide in chlorobenzene solvent.

Leon Segal in *Applied Spectroscopy* Vol. 17, No. 1, 1963 at pages 21–22, discloses the reaction of hexamethylene diamine in the solid state with atmospheric carbon dioxide.

Polyamine carbamates are useful as curing agents for elastomers. The primary diamine carbonates prepared by the process described herein are useful as intermediates for the preparation of polyamides.

SUMMARY OF THE INVENTION

This invention provides a process for the preparation of primary diamine carbamates which comprises reacting a liquid spray of primary diamine with gaseous carbon dioxide, in the optional presence of an inert propellant.

DETAILED DESCRIPTION OF THE INVENTION

The process of the present invention concerns the preparation of primary diamine carbamates by the spraying of a liquid primary diamine into carbon dioxide gas, optionally in the presence of an inert propellant. The diamine must be utilized above its melting point, i.e., in the liquid state. If the melting point of the diamine starting material lies above room temperature, or above whatever other temperature is chosen to be the temperature of the reaction, the diamine must first be heated above its melting temperature to allow for spraying.

The liquid diamine is propelled by pressure into the gaseous carbon dioxide, optionally using an inert gas, for example, but not limited to, nitrogen as a propellant.

Suitable diamines include primary aliphatic, cycloaliphatic, and aromatic diamines having 2–14 carbon atoms. The most preferred diamine is hexamethylene diamine. The melting point of industrially prepared, commercially available hexamethylene diamine is 39–40° C., and thus, the hexamethylene diamine must be heated above this temperature prior to reaction.

The process of the present invention avoids the problems of solvent handling prior to and during reaction and the effort associated with solvent removal from the diamine carbamate product that is required by some available processes and avoids the need for cryogenic grinding as required in other processes.

The process of the invention for primary aliphatic diamines may be summarized by the following equation for linear aliphatic primary diamines where x is a number from 2–14:

$$H_2N(CH_2)_xNH_2(liquid)+CO_2(gas) \rightarrow {}^+H_3N(CH_2)_xNHCOO^- (solid)$$

Spraying the molten amine into the carbon dioxide causes it to react vigorously, promptly, and completely. The diamine, the carbon dioxide or both may be mixed with an inert gas propellant to insure prompt and intimate contact between the diamine and the carbon dioxide. The spraying of the molten diamine in small droplets insures maximum contact surface and for the rapid reaction of diamine with the carbon dioxide.

In general, the smaller the droplet size, the easier it is to complete reaction. For each diamine employed, the optimum droplet size will vary. Optimum particle size for each diamine may be readily determined. Under optimum droplet size conditions, the reaction will be complete in a short time, essentially instantaneously.

It is, of course, necessary for the carbon dioxide to be present in the reaction zone in an amount at least stoichiometrically equal to the amount of diamine in order to achieve complete reaction. Usually carbon dioxide is present in the reaction mass in excess of the stoichiometric amount.

Carbon dioxide may be used at room temperature and may be used with an inert propellant such as nitrogen gas.

Representative amines that may be employed in the process of this invention include: 1,3-diaminopropane, 1,6-diaminohexane (hexamethylene diamine), 1,2-diaminoethane, 1,4-diaminobutane, 1,5-diaminopentane, 1,10-diaminodecane, 1,12-diaminododecane, 1,4-diaminocyclohexane, 4,4'-methylenebis(cyclohexylamine), 1,4-phenylenediamine, and 1,3-phenylenediamine. Preferred diamines are 1,6-diaminohexane (hexamethylene diamine), 1,12-diaminododecane and 4,4'-methylenebis(cyclohexylamine). Most preferred is 1,6-diaminohexane (hexamethylene diamine).

In the following example all parts and percentages are in parts by weight unless otherwise specified.

EXAMPLE 1

Preparation of Hexamethylene Diamine Carbamate

Hexamethylene diamine, 98.5% pure, 35 g, was charged to a 125 mL nitrogen pressurized atomizer. The hexamethylene diamine in the atomizer was heated by means of a hot water bath on a stirrer/hot plate to approximately 35° C. The outlet of the atomizer was directed toward the opening of a rectangular receiver constructed of corrugated paper board coated with a Teflon® fluoropolymer film. A stream of carbon dioxide gas from a laboratory sized cylinder was directed through a dispersing funnel at the rear of the hexamethylene diamine charged atomizer so as to encompass the hexamethylene diamine spray in a concurrent flow of carbon dioxide. The atomizer spray tip was indirectly heated with an infrared heat lamp to avoid a build up of hexamethylene diamine carbamate product. The carbon dioxide flow was started followed by startup of the hexamethylene diamine spray. The finely divided hexamethylene diamine droplets were instantly converted to a fine white powder that melting point determination (m.p. 150–160° C.) proved to be predominantly hexamethylene diamine carbamate.

What is claimed is:

1. A process for the preparation of primary diamine carbamates which comprises reacting a liquid spray of primary diamine with gaseous carbon dioxide, in the optional presence of an inert propellant.

2. The process of claim 1 in which the diamine is selected from the group consisting of aliphatic and cycloaliphatic diamines having 2–14 carbon atoms.

3. The process of claim 1 wherein the amine is selected from the group consisting of 1,2-diaminopropane, 1,6-diaminohexane (hexamethylene diamine), 1,2-diaminoethane, 1,4-diaminobutane, 1,5-diaminopentane, 1,10-diaminodecane, 1,12-diaminododecane, 1,4-diaminocyclohexane, 4,4'-methylenebis(cyclohexylamine), 1,4-phenylenediamine, and 1,3-phenylenediamine.

4. The process of claim 3 in which the amine is 1,6-diaminohexane (hexamethylene diamine).

5. The process of claim 3 in which the amine is 1,12-diaminododecane.

6. The process of claim 3 in which the amine is 4,4'-methylenebis(cyclohexylamine).

7. The process in claim 1 conducted in the presence of an inert propellant.

8. The process of claim 7 wherein the propellant is nitrogen gas.

* * * * *